(12) United States Patent
Fishman et al.

(10) Patent No.: US 11,291,681 B2
(45) Date of Patent: *Apr. 5, 2022

(54) METHOD FOR TREATING FIBROTIC LIVER TISSUE USING CL-IB-MECA

(71) Applicant: CAN-FITE BIOPHARMA LTD., Petach Tikva (IL)

(72) Inventors: Pnina Fishman, Petach Tikva (IL); Shira Cohen, Hod Hasharon (IL)

(73) Assignee: CAN-FITE BIOPHARMA LTD., Petach Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/003,191

(22) Filed: Aug. 26, 2020

(65) Prior Publication Data

US 2020/0384009 A1 Dec. 10, 2020

Related U.S. Application Data

(63) Continuation of application No. 15/986,332, filed on May 22, 2018, now Pat. No. 10,780,106, which is a continuation of application No. PCT/IL2016/051258, filed on Nov. 22, 2016.

(30) Foreign Application Priority Data

Nov. 23, 2015 (IL) .......................................... 242723

(51) Int. Cl.
| | |
|---|---|
| *A61K 31/7076* | (2006.01) |
| *A61P 1/16* | (2006.01) |
| *A61K 9/00* | (2006.01) |

(52) U.S. Cl.
CPC ........ *A61K 31/7076* (2013.01); *A61K 9/0053* (2013.01); *A61P 1/16* (2018.01)

(58) Field of Classification Search
None
See application file for complete search history.

(56) References Cited

U.S. PATENT DOCUMENTS

| | | | |
|---|---|---|---|
| 7,589,075 B2 | 9/2009 | Fishman et al. | |
| 8,846,635 B2 * | 9/2014 | Fishman | ................ A61P 43/00 514/45 |

FOREIGN PATENT DOCUMENTS

| | | |
|---|---|---|
| WO | 2009/050707 A1 | 4/2009 |
| WO | 2013/111132 A1 | 8/2013 |

OTHER PUBLICATIONS

Choi et al., "Cordyceps militaris alleviates non-alcoholic fatty liver disease in ob/ob mice", Nutrition Research and Practice, (2014), vol. 8, No. 2, pp. 172-176.
Nakamura et al., "Antitumor Effect of Cordycepin (3'-Deoxyadenosine) on Mouse Melanoma and Lung Carcinoma Cells Involves Adenosine A3 Receptor Stimulation", Anticancer Research, (2006), vol. 26, pp. 43-48.
Yoshikawa et al., "Cordyceps sinensis Acts as an Adenosine A3 Receptor Agonist on Mouse Melanoma and Lung Carcinoma Cells, and Human Fibrosarcoma and Colon Carcinoma Cells", Pharmacology & Pharmacy, (2011), vol. 2, pp. 266-270.
Cohen et al., "CF102 an A3 Adenosine Receptor Agonist Mediates Anti-Tumor and Anti-Inflammatory Effects in the Liver", Journal of Cellular Physiology, 2011, vol. 226, p. 2438-2447.
Stemmer et al., "Phase 1/2 of CF102, A Selective A3 Adenosine Receptor (A3AR) Agonist, In Patients with Hepatocellulae carcinoma (HCC)", European Journal of Cancer, (2010) Supplements, p. 122, 384 Poster.
Goodman, Journal of Hepatology 47 (2007) 598-607.

* cited by examiner

*Primary Examiner* — Layla D Berry
(74) *Attorney, Agent, or Firm* — Vorys, Sater, Seymour & Pease LLP; William Klima

(57) ABSTRACT

Provided is an $A_3AR$ ligand for reducing ectopic fat accumulation, particularly in fatty liver. Further provided is the use of $A_3AR$ ligand for the preparation of a pharmaceutical composition for reducing such fat accumulation, method of treating a condition associates with fat accumulation making use of the ligand and kits including pharmaceutical compositions including the ligand, and instructions for use of same, for treating a condition associated with ectopic fat accumulation. Further provided is the use of an $A_3AR$ agonist, such as 2-Chloro-$N^6$-(3-iodobenzyl)-adenosine-5'-N-methyluronamide (CI-IB-MECA, CF102) for treating fatty liver, specifically, non-alcoholic fatty liver disease (NAFLD).

8 Claims, 3 Drawing Sheets

METHOD FOR TREATING FIBROTIC LIVER TISSUE USING CL-IB-MECA

TECHNOLOGICAL FIELD

The present disclosure concerns medical uses of $A_3AR$ ligands.

BACKGROUND ART

References considered to be relevant as background to the presently disclosed subject matter are listed below:

International Patent Application Publication No. WO09/050707

International Patent Application Publication No. WO2013/111132

Acknowledgment of the above references herein is not to be inferred as meaning that these are in any way relevant to the patentability of the presently disclosed subject matter.

BACKGROUND

The Gi protein associated cell surface $A_3$ adenosine receptor ($A_3AR$), is over-expressed in cancer cells as well as in inflammatory cells and in peripheral blood mononuclear cells (PBMCs) derived from patients with various autoimmune inflammatory diseases, such as rheumatoid arthritis psoriasis and Crohn's Disease.

Activation of the Gi protein associated cell surface $A_3$ adenosine receptor ($A_3AR$) with highly specific ligands, such as the $A_3AR$ agonist 2-Chloro-$N^6$-(3-iodobenzyl)-adenosine-5'-N-methyluronamide (Cl-IB-MECA) was found to induce hepatocyte proliferation as disclosed in International Patent Application Publication No. WO09/050707.

In addition, International Patent Application Publication No. WO2013/111132 describes the use of Cl-IB-MECA for treatment of hepatocellular carcinoma (HCC) and for maintaining liver function in a subject having a chronic liver disease.

GENERAL DESCRIPTION

The present disclosure provides, in accordance with a first of its aspects an $A_3$ adenosine receptor ($A_3AR$) ligand for use in reducing ectopic lipid accumulation in a tissue of a subject.

The present disclosure provides, in accordance with a second aspect, a method for reducing ectopic lipid accumulation in a tissue of a subject, the method comprising administering to said subject an amount of $A_3AR$ ligand.

The present disclosure provides, in accordance with a third aspect, the use of an $A_3AR$ ligand for the preparation of a pharmaceutical composition for reducing ectopic lipid accumulation.

Further, the present disclosure provides, in accordance with a fourth aspect, a pharmaceutical composition comprising a pharmaceutically acceptable carrier and as active ingredient an $A_3AR$ ligand in an amount effective to reduce ectopic lipid accumulation in a tissue of a subject.

Finally, the present disclosure provides, in accordance with its fifth aspect, a kit comprising a pharmaceutical composition comprising an $A_3AR$ ligand and instructions for use of the pharmaceutical composition for in reducing ectopic lipid accumulation in a tissue of a subject.

In some embodiments, the $A_3AR$ ligand is used for reducing fat accumulation in the liver.

In some further embodiments, the $A_3AR$ ligand is an the $A_3AR$ agonist, preferably 2-chloro-$N^6$-(3-iodobenzyl)-adenosine-5'-N-methyluronamide (Cl-IB-MECA, herein also referred to as CF102) for use in treating fat accumulation in the liver or a condition associated with fat accumulation in the liver of a subject.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

Figure 4:
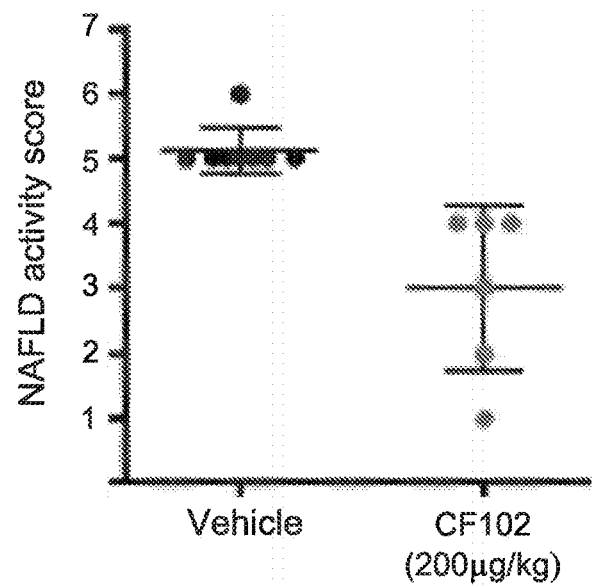
FIG. 4 is a graph showing the decrease in NAFLD activity score following treatment with CF102 at a concentration of 200 µg/kg.
Figure 5:
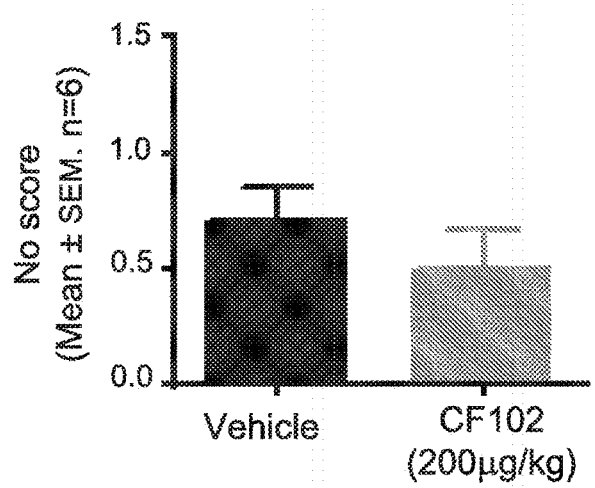
FIG. 5 is a graph showing the effect of CF102, at a concentration of 200 µg/kg, in reducing the inflammation NAS score compared to the vehicle.

The present disclosure is based on the finding that 2-chloro-$N^6$-(3-iodobenzyl)-adenosine-5'-N-methyluronamide (Cl-IB-MECA, herein also referred to as CF102), an $A_3$ adenosine receptor ($A_3AR$) agonist, with high affinity and selectivity to the $A_3AR$, induced improvement of non-alcoholic fatty liver disease (NAFLD) in a murine experimental model. This unexpected improvement was exhibited, inter alia, by the reduction of liver to body weight ratio in nonalcoholic steatohepatitis (NASH) livers, by the decrease in triglycerides level in the liver and most importantly, by the NAFLD score considered the endpoint (FIG. 4) and by the reduction in NAS inflammation score as compared to the control vehicle (FIG. 5).

Based on these findings, it has been concluded by the inventors that an activator of the $A_3AR$, be it an $A_3AR$ agonist or an $A_3AR$ allosteric enhancer, is an effective tool for reducing fat/lipid accumulating in ectopic sites, particularly and preferably in the liver.

Thus, in accordance with a first of its aspects, the present disclosure provides an $A_3AR$ ligand for use in reducing ectopic fat accumulation in a tissue of a subject having a condition associated with such fat accumulation, e.g. non-alcoholic fatty liver disease (NAFLD) or specifically non-alcoholic steatohepatitis (NASH).

In the following description when referring to the $A_3AR$ ligand for use in reducing ectopic lipid accumulation, it is to be understood as also encompassing a method for reducing ectopic lipid accumulation by the administration of the $A_3AR$ ligand; to the use of the $A_3AR$ ligand for the preparation of a pharmaceutical composition for reducing ectopic lipid accumulation; to a pharmaceutical composition comprising a pharmaceutically acceptable carrier and as active ingredient an A$_3$AR ligand in an amount effective to reduce e lipid accumulation; and to a kit comprising the pharmaceutical composition, and instructions for use of the composition for reducing ectopic lipid accumulation.

In the context of the present disclosure, when referring to lipid accumulation it is to be understood as equivalently referring to fat accumulation. In the context of the present invention ectopic fat accumulation is used to denote deposition or storage of lipids, especially triglycerides in tissues and/organs other than adipose tissue, i.e. that under normal (healthy) conditions lack lipid cells (lipocytes/fat cells). Ectopic fat deposition is recognized as fat accumulation in the abdominal regions (as opposed to subcutaneous/peripheral fat deposition) and is known to occur in the liver, skeletal muscle, heart and pancreas. Ectopic fat deposition is undesired and can cause health complications, such as insulin resistance, and thus its prevention or reduction is desired.

In a preferred embodiment, the A$_3$AR ligand is used for reducing lipid accumulation in the liver.

In some embodiments, the reduction of lipid accumulation is in a population of subjects being diagnosed as suffering from NAFLD and/or NASH.

It is noted that NAFLD does not necessarily involve inflammation and it may be that a fatty liver remains free of inflammation. It is further noted that in fatty liver, the liver functions normally and looks normal under the microscope, except for accumulations of fat within cells. In addition, in NAFLD liver blood tests are typically either normal, or there may be some slight increases in two of the enzymes made by the liver, the serum ALT (alanine aminotransferase) and/or the serum AST (aspartate aminotransferase).

The fat typically accumulating under condition of ectopic fat accumulation includes, without being limited thereto, glycerides (monoglycerides, diglycerides, triglycerides) and at times also sterols such as cholesterol.

In one embodiment, the reduction of lipid deposits is exhibited by at least reduction in level of triglycerides (TG) in the tissue. In this context, reduction in level of TG is to be determined as significant under medical parameters. This may include, at times, at least 5% reduction in the level of TG as compared to the level thereof in at least one earlier measurement time point (e.g. one or more days, weeks or months).

When the lipid deposited tissue is the liver, the reduction of lipid deposition can also be exhibited by one of the following:

reduction in liver-to-body weight ratio;
reduced alanine aminotransferase (ALT) levels;
reduction in NAS score of inflammation.

In one embodiment, the A$_3$AR ligand is used for treating non-alcoholic fatty liver disease (NAFLD).

NAFLD is a condition in which fat accumulates in the liver of a patient without a history of alcohol abuse. NAFLD is classified into simple steatosis and nonalcoholic steatohepatitis (NASH). In NASH, not only steatosis but also intralobular inflammation and hepatocellular ballooning are present, often accompanied by progressive fibrosis. In the context of the present disclosure, any one of the above are treating, i.e. simple steatosis, nonalcoholic steatohepatitis (NASH), intralobular inflammation, hepatocellular ballooning, progressive fibrosis, each constituting an independent embodiment in accordance with the present disclosure.

Long-standing NASH may progress to liver cirrhosis, and hepatocellular carcinoma (HCC) may be an outcome. Therefore, in some embodiments, by the treatment of NAFLD, or specifically, NASH, the present disclosure provides prevention of liver diseases, such as, liver cirrhosis, and hepatocellular carcinoma (HCC).

Accordingly, in one embodiment, the present disclosure provides the use of the A$_3$AR ligand for preventing liver disease in a subject being in predisposition of developing said liver disease. The predisposition of the subject to develop a liver disease is determined by the presence of fat accumulated in the liver or the existence of NAFLD.

In the context of the present disclosure "A$_3$ adenosine receptor ligand" or "A$_3$AR ligand" denotes any compound capable of directly (e.g. via the receptor binding site) or indirectly (e.g. via an allosteric binding site) enhance the activity of the A$_3$ adenosine receptor, this including full or partial activation of the A$_3$ adenosine receptor. The A$_3$AR ligand is thus a molecule that exerts its prime effect through the enhancement of the activity of the A$_3$AR irrespective of whether the activation is via the binding site or allosteric binding site. This means that at the doses it is being administered it essentially affects only the A$_3$AR.

In one embodiment, the "A$_3$ adenosine receptor ligand" is an A$_3$AR agonist.

In one other embodiment, the "A$_3$ adenosine receptor ligand" is an A$_3$AR allosteric enhancer.

When referring to "A$_3$ adenosine receptor agonist" or "A$_3$AR agonist" it is to be understood to mean any ligand capable of specifically binding to the A$_3$ adenosine receptor, thereby fully or partially activating the A$_3$ adenosine receptor. The A$_3$AR agonist is thus a molecule that exerts its prime effect through the binding and activation of the A$_3$AR. This means that at the doses it is being administered it essentially binds to and activates only the A$_3$AR.

In one embodiment, an A$_3$AR agonist has a binding affinity (K$_i$) to the human A$_3$AR in the range of less than 100 nM, typically less than 50 nM, preferably less than 20 nM, more preferably less than 10 nM and ideally less than 5 nM. Particularly preferred are A$_3$AR agonists that have a K$_i$ to the human A$_3$R of less than 2 nM and desirably less than 1 nM.

However, it should be understood that some A$_3$AR agonists can also interact with and activate other receptors, however, with lower affinities (namely a higher Ki).

A molecule will be considered an A$_3$AR agonist in the context of the present disclosure (namely a molecule that exerts its prime effect through the binding and activation A$_3$AR) if its affinity to the A$_3$AR is at least 3 times (i.e. its Ki to the A$_3$AR is at least 3 times lower), preferably 10 times, desirably 20 times and most preferably at least 50 times larger than the affinity to any other of the adenosine receptors (i.e. A$_1$, A$_{2a}$ and A$_{2b}$).

The affinity of an A$_3$AR agonist to the human A$_3$AR as well as its relative affinity to the other human adenosine receptors can be determined by a number of assays, such as a binding assay. Examples of binding assays include providing membranes containing a receptor and measuring the ability of the A$_3$AR agonist to displace a bound radioactive agonist; utilizing cells that display the respective human adenosine receptor and measuring, in a functional assay, the ability of the A$_3$AR agonist to activate or deactivate, as the case may be, downstream signaling events such as the effect on adenylate cyclase measured through increase or decrease of the cAMP level; etc. If the administered level of an A$_3$AR agonist is increased such that its blood level reaches a level approaching that of the Ki of the A$_1$, A$_{2a}$ and A$_{2b}$ adenosine receptors, activation of these receptors may occur following such administration, in addition to activation of the A$_3$AR.

An A$_3$AR agonist is thus preferably administered at a dose such that the blood level is such so that essentially only the A$_3$AR will be activated.

In one embodiment, the A$_3$AR agonist is a molecule that has a purine backbone. In some embodiment, the purine containing compound may be determined as an A$_3$AR agonist based on acceptable structure-function activity assays.

The characteristic of some A$_3$AR agonists and methods of their preparation are described in detail in, inter alia, U.S. Pat. Nos. 5,688,774; 5,773,423, 5,573,772, 5,443,836, 6,048,865, WO 95/02604, WO 99/20284, WO 99/06053, WO 97/27173 and WO 01/19360, all of which are incorporated herein by reference.

According to some embodiments of the present disclosure, the A$_3$AR agonist is a purine derivative falling within the scope of the general formula (I):

wherein,

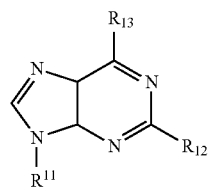

(I)

R$_{11}$ represents an alkyl, hydroxyalkyl, carboxyalkyl or cyanoalkyl or a group of the following general formula (II):

in which:

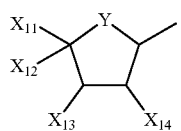

(II)

Y represents oxygen, sulfur or CH$_2$;

X$_{11}$ represents H, alkyl, R$^e$R$^f$NC(=O)— or HOR$^g$—, wherein

R$^e$ and R$^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and R$^g$ is selected from the group consisting of alkyl, amino, haloalkyl, aminoalkyl, BOC-aminoalkyl, and cycloalkyl;

X$_{12}$ is H, hydroxyl, alkylamino, alkylamido or hydroxyalkyl;

X$_{13}$ and X$_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both X$_{13}$ and X$_{14}$ are oxygens connected to >C=S to form a 5-membered ring, or X$_{12}$ and X$_{13}$ form the ring of formula (III):

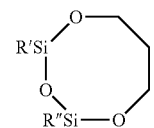

(III)

where R' and R" represent independently an alkyl group;

R$_{12}$ is selected from the group consisting of hydrogen, halo, alkylether, amino, hydrazido, alkylamino, alkoxy, thioalkoxy, pyridylthio, alkenyl; alkynyl, thio, and alkylthio; and R$_{13}$ is a group of the formula —NR$_{15}$R$_{16}$ wherein R$_{15}$ is a hydrogen atom or a group selected from alkyl, substituted alkyl or aryl-NH—C(Z)—, with Z being O, S, or NR$^a$ with R$^e$ having the above meanings; wherein when R$_{15}$ is hydrogen than R$_{16}$ is selected from the group consisting of R— and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, fururyl, L-propylalanyl-aminobenzyl, β-alanylamino-benzyl, T-BOC-β-alanylaminobenzyl, phenylamino, carbamoyl, phenoxy or cycloalkyl; or R$_{16}$ is a group of the following formula (IV):

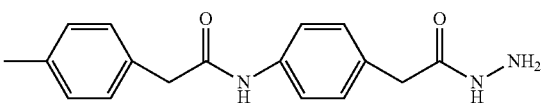

(IV)

or when R$_{15}$ is an alkyl or aryl-NH—C(Z)—, then, R$_{16}$ is selected from the group consisting of heteroaryl-NR$^a$—C(Z)—, heteroaryl-C(Z)—, alkaryl-NR$^a$—C(Z)—, alkaryl-C(Z)—, aryl-NR—C(Z)— and aryl-C(Z)—; Z representing an oxygen, sulfor or amine.

Exemplary A$_3$AR agonist (disclosed in U.S. Pat. No. 5,688,774 at column 4, lines 67-column 6, line 16; column 5, lines 40-45; column 6, lines 21-42; column 7, lines 1-11; column 7, lines 34-36; and column 7, lines 60-61):

N$^6$-(3-iodobenzyl)-9-methyladenine;
N$^6$-(3-iodobenzyl)-9-hydroxyethyladenine;
R—N$^6$ (3-iodobenzyl)-9-(2,3-dihydroxypropyl)adenine;
S—N$^6$-(3-iodobenzyl)-9-(2,3-dihydroxypropyeadenine;
N$^6$-(3-iodobenzyladenin-9-yl)acetic acid;
N$^6$-(3-iodobenzyl)-9-(3-cyanopropyl)adenine;
2-chloro-N$^6$-(3-iodobenzyl)-9-methyladenine;
2-amino-N$^6$-(3-iodobenzyl)-9-methyladenine;
2-hydrazido-N$^6$-(3-iodobenzyl)-9-methyladenine;
N$^6$-(3-iodobenzyl)-2-methylamino-9-methyladenine;
2-dimethylamino-N$^6$-(3-iodobenzyl)-9-methyladenine;
N$^6$-(3-iodobenzyl)-9-mcthyl-2-propylaminoadenine;
2-hexyl amino-N$^6$-(3-iodobenzyl)-9-methyladenine;
N$^6$-(3-iodobenzyl)-2-methoxy-9-methyladenine;
N$^6$-(3-iodobenzyl)-9-methyl-2-methylthioadenine;
N$^6$-(3-iodobenzyl)-9-methyl-2-(4-pyridylthio)adenine;
(1S, 2R, 3S, 4R)-4-(6-amino-2-phenylethylamino-9H-purin-9-yl)cyclopentane-1,2,3-triol;
(1S, 2R, 3S, 4R)-4-(6-amino-2-chloro-9H-purin-9-yl)cyclopentane-1,2,3-triol;

(±)-9-[2α,3α-dihydroxy-4β-(N-methylcarbamoyl)cyclopent-1β-yl)]-N⁶-(3-iodobenzyl)-adenine;
2-chloro-9-(2'-amino-2',3'-dideoxy-β-D-5'-methyl-arabino-furonamido)-N⁶-(3-iodobenzyl)adenine;
2-chloro-9-(2',3'-dideoxy-2'-fluoro-β-D-5'-methyl-arabino furonamido)-N⁶-(3-iodobenzyl)adenine;
9-(2-acetyl-3-deoxy-β-D-5-methyl-ribofuronamido)-2-chloro-N⁶(3-iodobenzyl)adenine;
2-chloro-9-(3-deoxy-2-methanesulfonyl-β-D-5-methyl-ribofuronamido)-N⁶-(3-iodobenzyl)adenine;
2-chloro-9-(3-deoxy-β-D-5-methyl-ribofuronamido)-N⁶-(3-iodobenzyl)adenine;
2-chloro-9-(3,5-1,1,3,3-tetraisopropyldisiloxyl-β-D-5-ribofuranosyl)-N⁶-(3-iodobenzyl)adenine;
2-chloro-9-(2',3'-O-thiocarbonyl-β-D-5-methyl-ribofuranamido)-N⁶-(3-iodobenzyl)adenine;
9-(2-phenoxythiocarbonyl-3-deoxy-β-D-5-methyl-ribofuronamido)-2-chloro-N⁶-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-N⁶ benzyladenine;
2-chloro-9-(2'-azido-2',3'-dideoxy-β-D-5'-methyl-arabino-furonamido)-N⁶-benzyladenine;
2-chloro-9-(β-D-erythrofuranoside)-N⁶-(3-iodobenzyl)adenine;
N⁶-(benzodioxanemethyl)adenosine;
1-(6-furfurylamino-9H-purin-9-yl)-1-deoxy-N-methyl-β-D-ribofuranosiduronamide;
N⁶-[3-(L-prolylamino)benzyl]adenosine-5'-N-methyluronamide;
N⁶-[3-(β-alanylamino)benzyl]adenosine-5'-N-methyluronamide;
N⁶-[3-(N-T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-N⁶-[(3-β-alanylamino)benzyl]adenosine;
9-(β-D-erythrofuranoside)-2-methylamino-N⁶-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

Other exemplary A₃AR agonists, disclosed in U.S. Pat. No. 5,773,423, are compounds of the formula (V):

$X_1$ is $R^a R^b NC(=O)$ wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R— and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific compounds include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific compounds are those compounds wherein $R^a$ is hydrogen and $R_2$ is hydrogen, particularly when $R_5$ is unsubstituted benzyl.

More specific compounds are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those compounds where $R^a$ is hydrogen, $R^b$ is $C_1$-$C_{10}$ alkyl or $C_3$-$C_{10}$ cycloalkyl, and $R_5$ is R— or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

An example of an especially preferred compound disclosed in U.S. Pat. No. 5,773,423 is N⁶-(3-iodobenzyl)-2-methylamino-9-[5-(methylamido)-β-D-ribofuranosyl]-adenine, also known as N⁶-(3-iodobenzyl)-adenosine-5'-N-methyluronamide or known as 1-Deoxy-1-[6-[[(3-iodophenyl)methyl]amino]-9H-purine-9-yl]-N-methyl-D-ribofuranuronamide, or by the abbreviation IB-MECA.

In addition, those compounds in which $R_2$ is a $C_2$-$C_{10}$ alkenylene of the formula $R^d$—C=C— where $R^d$ is a $C_1$-$C_8$ alkyl are also particularly noted in U.S. Pat. No. 5,773,423.

Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Further exemplary A₃AR agonists disclosed in U.S. Pat. No. 5,773,423 are modified xanthine-7-ribosides having the formula (VI):

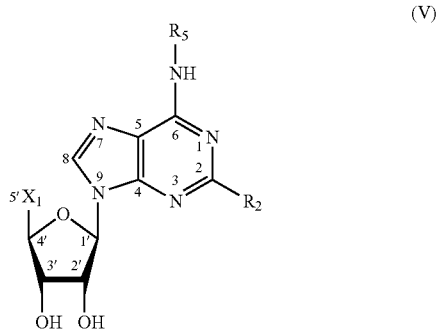

(V)

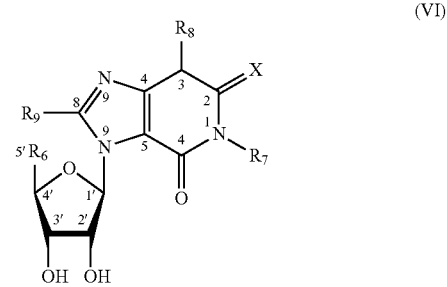

(VI)

wherein wherein
X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R— and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkyl.

WO 99/06053 discloses in examples 19-33 compounds selected from:

$N^6$-(4-biphenyl-carbonylamino)-adenosine-5'-N-ethyluronamide:

$N^6$-(2,4-dichlorobenzyl-carbonylamino)-adenosine-5'-N-ethyluronamide;

$N^6$-(4-methoxyphenyl-carbonylamino)-adenosine-5'-N-ethyluronamide;

$N^6$-(4-chlorophenyl-carbonylamino)-adenosine-5'-N-ethyluronamide;

$N^6$-(phenyl-carbonylamino)-adenosine-5'-N-ethyluronamide;

$N^6$-(benzylcarbamoylamino)-adenosine-5'-N-ethyluronamide;

$N^6$-(4-sulfonamido-phenylcarbamoyl)-adenosine-5'-N-ethyluronamide;

$N^6$-(4-acetyl-phenylcarbamoyl)-adenosine-5'-N-ethyluronamide;

$N^6$-((R)-α-phenylethylcarbamoyl)-adenosine-5'-N-ethyluronamide;

$N^6$-((S)-α-phenylethylcarbamoyl)-adenosine-5'-N-ethyluronamide;

$N^6$-(5-methyl-isoxazol-3-yl-carbamoyl)-adenosine-5'-N-ethyluronamide;

$N^6$-(1,3,4-thiadiazol-2-yl-carbamoyl)-adenosine-5'-N-ethyluronamide;

$N^6$-(4-n-propoxy-phenylcarbamoyl)-adenosine-5'-N-ethyluronamide;

$N^6$-bis-(4-nitrophenylcarbamoyl)-adenosine-5'-N-ethyluronamide; and $N^6$-bis-(5-chloro-pyridin-2-yl-carbamoyl)-adenosine-5'-N-ethyluronamide.

More specifically disclosed compounds include:

2-chloro-$N^6$-(3-iodobenzyl)-9-[5-(methylamido)-β-D-ribofuranosyl]-adenine also known as 2-chloro-$N^6$-(3-iodobenzyl)-adenosine-5'-N-methyluronamide or by the abbreviation Cl-IB-MECA;

$N^6$-(3-iodobenzyl)-2-methylamino-9-[5-(methylamido)-β-D-ribofuranosyl]-adenine, also known as $N^6$-(3-iodobenzyl)-adenosine-5'-N-methyluronamide or known as 1-Deoxy-1-[6-[[(3-iodophenyl)methyl]amino]-9H-purine-9-yl]-N-methyl-D-ribofuranuronamide or by the abbreviation IB-MECA;

$N^6$-2-(4-aminophenyl)ethyladenosine (APNEA);

$N^6$-(4-amino-3-iodobenzyl) adenosine-5'-(N-methyluronamide) (AB-MECA).

In one particular embodiment, Cl-IB-MECA is used in reducing ectopic lipid accumulation, accordance with the present disclosure.

When referring to "$A_3$AR allosteric enhancement" it is to be understood as referring to the positive regulation, activation or incense of the receptor activity by binding of the allosteric effector molecule at the receptor's allosteric site which may be different from the binding site of the endogenous ligand or agonist thereof.

In one embodiment, "enhancement" denotes an effect of the effector compound on the receptor exhibited by an increase of at least 15% in the efficacy of the $A_3$ adenosine receptor by binding of the effector compound to the allosteric site of the receptor and/or by a decrease in dissociation rate of adenosine or an $A_3$AR agonist to the orthosteric binding site.

In one embodiment, the enhancement is by an "$A_3$AR allosteric enhancer" or "$A_3$ARAE" that is an imidazoquinoline derivative.

In one embodiment the $A_3$AR enhancer, or imidazoquinoline derivative has the following general formula (VII):
wherein:

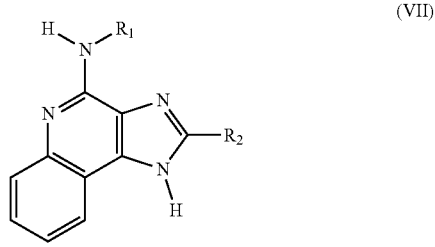

(VII)

$R_1$ represents an aryl or alkaryl being optionally substituted at the aromatic ring with one or more substituents selected from the group consisting of $C_1$-$C_{10}$ alkyl, halo, $C_1$-$C_{10}$ alkanol, hydroxyl, $C_1$-$C_{10}$ acyl, $C_1$-$C_{10}$ alkoxyl; $C_1$-$C_{10}$-alkoxycarbony, $C_1$-$C_{10}$ alkoxylalkyl; $C_1$-$C_{10}$ thioalkoxy; $C_1$-$C_{10}$ alkylether, amino, hydrazido, $C_1$-$C_{10}$ alkylamino, pyridylthio, $C_2$-$C_{10}$ alkenyl; $C_2$-$C_{10}$ alkynyl, thio, $C_1$-$C_{10}$ alkylthio, acctoamido, sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;

$R_2$ represents hydrogen or a substituent selected from the group consisting of $C_1$-$C_{10}$ alkyl, $C_2$-$C_{10}$ alkenyl; $C_2$-$C_{10}$ alkynyl, $C_4$-$C_{10}$ cycloalkyl, $C_4$-$C_{10}$ cycloalkenyl, a five to seven membered heterocyclic aromatic ring, $C_5$-$C_{15}$ fused cycloalkyl, bicyclic aromatic or heteroaromatic rings; $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, and $C_1$-$C_{10}$ alkylthio, acetoamido and sulfonic acid;

and pharmaceutically acceptable salts thereof.

According to some embodiments, the $R_1$ substituent in the $A_3$ARAE has the following general formula (VIII):

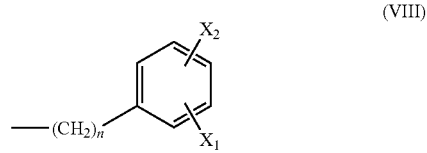

(VIII)

wherein n is 0 or an integer selected from 1-5; preferably, n is 0, 1 or 2; and $X_1$ and $X_2$ which may be the same or different, are selected from hydrogen halogen, alkyl, alkanol or alkoxy, indanyl, pyrroline provided that when said n is 0, $X_1$ and $X_2$ are not hydrogen.

In yet some further embodiments, $R_1$ in $A_3ARAE$ is a substituent having the above formula (VIII), wherein $X_1$ or $X_2$, which may be the same or different, are selected from hydrogen, chloro, methoxy, methanol or a substituent having the formulae (VIIIa) or (VIIIb):

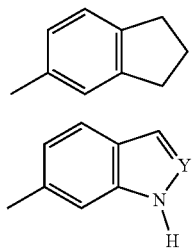

(VIIIa)

(VIIIb)

wherein Y is selected from N or CH.

In some yet further embodiments $R_2$ in $A_3ARAE$ is selected from H, $C_{1-10}$ alkyl, $C_{4-10}$ cycloalkyl, the alkyl chain may be a straight or branched or form a four to seven membered cycloalkyl ring.

In one embodiment, $R_2$ in $A_3ARAE$ is selected from a five to seven membered heterocyclic aromatic ring.

In some embodiments, $R_2$ substituents in $A_3ARAE$ are selected from H, n-pentyl, or a five membered heterocyclic aromatic ring having the following formula (IX):

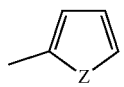

(IX)

wherein Z is selected from O, S or NH, preferably O.

In accordance with one embodiment $R_2$ in $A_3ARAE$ comprises one or more fused rings, particularly so as to form bicyclic substituents.

Non-limiting examples of hicyclic compounds which may be used to form the substituents in the context of the invention comprise bicyclo[2.2.1]heptane, bicyclo[4.1.0] heptane, bicyclo[4.1.0]heptan-3-carboxylic acid, bicyclo [3.1.0]hexan-3-carboxylic acid, bicyclo[4.1.0]heptan-2-carboxylic acid, bicyclo[3.1.0]hexan-2-carboxylic acid, and bicyclo[2.2.1]heptan-2-carboxylic acid.

In accordance with yet some other embodiments, $R_2$ in $A_3ARAE$ may be selected from 2-cyclohexene and 3-cyclohexene.

Specific imidazoquinoline derivatives which may be used as allosteric effectors of the $A_3AR$ are listed below:

N-(4-Methyl-phenyl)-2-cyclopentyl-1H-imidazo[4,5-c]quinolin-4-amine

N-(4-Methoxy-phenyl)-2-cyclopentyl-1H-imidazo[4,5-c] quinolin-4-amine

N-(3,4-Dichloro-phenyl)-2-cyclopentyl-1H-imidazo[4,5-c] quinolin-4-amine

N-(4-Chloro-phenyl)-2-cyclopentyl-1H-imidazo[4,5-c]quinolin-4-amine

N-(3-Methanol-phenyl)-2-cyclopentyl-1H-imidazo[4,5-c] quinolin-4-amine

N-([3,4-c]Indan)-2-cyclopentyl-1H-imidazo[4,5-c]quinolin-4-amine

N-(1H-indazol-6-yl)-2-cyclopentyl-1H-imidazo[4,5-c]quinolin-4-amine

N-(4-Methoxy-benzyl)-2-cyclopentyl-1H-imidazo[4,5-c] quinolin-4-amine

N-(1H-Indol-6-yl)-2-cyclopentyl-1H-imidazo[4,5-c]quinolin-4-amine

N-(Benzyl)-2-cyclopentyl-1H-imidazo[4,5-c]quinolin-4-amine

N-(Phenylethyl)-2-cyclopentyl-1H-imidazo[4,5-c]quinolin-4-amine

N-(3,4-Dichloro-phenyl)-2-cycloheptyl-1H-imidazo[4,5-c] quinolin-4-amine

N-(3,4-Dichloro-phenyl)-2-furyl-1H-imidazo[4,5-c]quinolin-4-amine

N-(3,4-Dichloro-phenyl)-2-cyclobutyl-1H-imidazo[4,5-c] quinolin-4-amine

N-(3,4-Dichloro-phenyl)-2-cyclohexyl-1H-imidazo[4,5-c] quinolin-4-amine

N-(3,4-Dichloro-phenyl)-2-1H-imidazo[4,5-c]quinolin-4-amine

N-(3,4-Dichloro-phenyl)-2-pentyl-1H-imidazo[4,5-c]quinolin-4-amine.

The above imidazoquinoline derivatives are regarded as allosteric effectors (modulating the activity) as they were shown to have, on the one hand, reduced affinity, if any, to the orthosteric binding sites of the $A_1$ and $A_{2A}$, $A_{2B}$ adenosine receptors and reduced affinity to the orthosteric binding site of the $A_3$ adenosine receptor, and on the other hand, high affinity to the allosteric site of the $A_3$ adenosine receptor [International Patent Application No. WO07/089507, incorporated herein by reference].

A specifically preferred imidazoquinoline derivative in accordance with the present disclosure is N-(3,4-Dichloro-phenyl)-2-cyclohexyl-1H-imidazo[4,5-c]quinolin-4-amine (also referred to at times by the abbreviation LUF6000 or CF602), being an allosteric enhancer.

In the context of the general formulae disclosed herein, the following meaning for the various terms is to be considered:

The term "alkyl" is used herein to refer to a linear or branched hydrocarbon chain having from 1 to 10 carbon atoms and more preferably 1 to 6 carbon atoms including, but not limited to, methyl, ethyl, n-propyl, isopropyl, n-butyl, t-butyl, n-heptyl, octyl and the like.

Similarly, the terms "alkenyl" and "alkynyl" denote a linear or branched hydrocarbon chain having, respectively, from 2 to 10, or from 3 to 10 carbon atoms and more preferably 2 to 6 or 3 to 6 carbon atoms, the alkenyl or alkynyl having at least one unsaturated bond.

The alkyl, alkenyl or alkynyl substituents may be substituted with a heteroatom containing group. Thus, it should be understood that while not explicitly stated, any of the alkyl modifications defined hereinabove and below, such as alkylthio, alkoxy, akanol, alkylamine etc, also include the corresponding alkenyl or alkynyl modifications, such as, akenylthio, akenyloxy, alkenol, alkenylamine, or respectively, akynylthio, alkynyloxy, alkynol, alkynylamine.

The term "aryl" denotes an unsaturated aromatic carbocyclic group of from 5 to 14 carbon atoms having a single ring (e. g., phenyl) or multiple condensed rings (e. g., naphthyl or anthryl). Preferred aryls include phenyl, indanyl, benzimidazole.

The term "alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl and the like.

The term "Substituted aryl" refers to an aromatic moiety which is substituted with from 1 to 3 substituents as defined above. A variety of substituents are possible, as appreciated by those versed in the art. Nonetheless, some preferred substituents include, without being limited thereto, halogen, (substituted) amino, nitro, cyano, alkyl, alkoxy, acyloxy or alkanol, sulphonyl, sulphynyl.

The term "Halo" or "halogen" refers to fluoro, chloro, bromo and iodo, preferably to chloro.

The term "acyl" refers to the groups H—C(O)— as well as alkyl-C(O)—.

The term "alkanol" refers to the group —COH as well as alk-OH, "alk" denoting an alkylene, alkenylene or alkynylene chain.

The term "alkoxy" is used herein to mean —O-alkyl, including, but not limited to, methoxy, ethoxy, propoxy, isopropoxy, n-butoxy and the like.

The term "alkylthio" is used herein to mean —S-alkyl, including, but not limited to, methylthio, ethylthio, n-propylthio, isopropylthio, n-butylthio and the like.

The term "alkoxyalkyl" is used herein to mean -alkyl-O-alkyl, including, but not limited to, methoxymethyl, ethoxymethyl, n-propoxymethyl, isopropoxymethyl, n-butoxymethyl, isobutoxymethyl, t-butoxymethyl and the like.

The term "cycloalkyl" is used herein to mean cyclic hydrocarbon radicals including, but not limited to, cyclopropyl, cyclobutyl, cyclopentyl, cyclohexyl, cycloheptyl and the like.

The term "alkoxycarbonyl" is used herein to mean —C(O)O-alkyl, including, but not limited to, methoxycarbonyl, ethoxycarbonyl, propoxycarbonyl and the like.

The term "fused cycloalkyl" is used herein to mean any compound or substituent comprising at least two aliphatic rings which are connected at a single atom (to form a spirocyclic moiety), at two mutually bonded atoms or across a sequence of atoms (bridgehead). The fused rings may include any bicyclic, tricyclic as well as polycyclic moieties. Bicyclic substituents are preferred in accordance with some embodiments of the present disclosure.

The present disclosure also makes use of physiologically acceptable salts of an $A_3AR$ ligand, such as the above disclosed compounds. An "physiologically acceptable salts" refers to any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the ligand with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

The $A_3AR$ ligand can be administered in a single dose (one time medication) or as a continuous treatment, for over a period of days, weeks or even months.

In one embodiment, the $A_3AR$ ligand is used for long term treatment. In the context of the present disclosure, long term treatment is to be understood to encompassing a treatment window lasting for at least days, weeks, or months, until, for example, no medically significant level of lipid is detected at the site where lipid accumulation was detected before treatment began. Further in the context of the present disclosure long term treatment can encompass chronic treatment, e.g. long term administration without an envisaged treatment end time point. In some embodiments, the long term treatment comprises at least one week of daily administration of the ligand, at times, one month treatment, at times, at least 2, 3, 4, 5, 6, or even 12 months of daily administration of the ligand.

When referring to "treatment" by the $A_3AR$ ligand it is to be understood to refer to any desired pharmacological and physiological effect that leads to medically significant improvement in the subject's conditions as determined by parameters known to those versed in the art. For example, an improvement can be determined by a decrease in at least 5% in the level of triglycerides at the target site (site of deposited fat).

In one additional or alternative embodiment, improvement can be determined by reduction in the target site to body weight ratio (e.g. liver to body weight ratio).

In yet one other or additional embodiment, improvement can be determined by a change in one or more parameters indicative of the functionality of the target organ. For example, when the target site is the liver, improvement can be determined by decrease in ALT levels.

Further, in one other embodiment, improvement can be determined by the reduction in NAS score of inflammation. NAS score is determined by various components referred to as the NAFLD Activity Score (NAS) and Fibrosis Staging. These include, inter alia, steatosis score, lobular inflammation score, hepatocyte ballooning and fibrosis. Total NAS score represents the sum of scores for steatosis, lobular inflammation, and ballooning, and ranges from 0-8. NAS scores of 0-2 are considered not diagnostic of NASH and scores of 5-8 are considered diagnostic of NASH.

In some embodiments, the treatment is of a subject that is defined as suffering from a condition associated with fat accumulation.

The $A_3AR$ ligand can be administered on a daily basis or with a day or more intervals between administrations. In one embodiment, $A_3AR$ ligand is used on a daily basis, for chronic treatment.

The $A_3AR$ ligand can be administered systemically or locally. To this end, the $A_3AR$ ligand is combined with pharmaceutically acceptable carries to form a pharmaceutical composition suitable for a specific mode of administration and comprising an effective amount of the $A_3AR$ ligand.

By the term "pharmaceutically acceptable carrier" it is meant any one of inert, non-toxic materials, which do not react with the $A_3AR$ ligand and which can be added to the ligand to facilitate its delivery to subject.

In one embodiment, the carrier is one that is acceptable for preparation of a unit dosage form for oral administration.

An oral formulation may be in the form of a pill, capsule, in the form of syrup, emulsion, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the $A_3AR$ ligand, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Typical examples of carriers suitable for oral administration comprise (a) suspensions or emulsions in an appropriate liquid such as Cremophor RH40, or methylcellulose (e.g. Methocel A4M Premium); (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the tragacanth as solids or granules; (c) powders; (d) solution, typically when combined with a solubilizing enhancing agent; (e) liposome formulation; and others.

The $A_3AR$ ligand is used in an amount effective to treat the fat accumulation, namely, an amount which exhibits an effect of reducing lipid depositing in tissues which do not normally (under healthy condition) harbor such fat cells, the reduction being compared between two time points, at least one after the ligand consumption. The "effective amount" can be readily determined, in accordance with the present disclosure, by administering to a plurality of tested subjects various amounts of the $A_3AR$ ligand and then plotting the response (for example combining several beneficial effects) as a function of the amount. At times, the amount to be used may depend on a variety of factors such as mode of administration, age, weight, body surface area, gender, health condition and genetic factors of the subject; other administered drugs; etc.

The effective amount of the $A_3AR$ ligand can be defined by a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

When the $A_3AR$ ligand is an $A_3AR$ agonist, the effective amount may, for example, be an amount of at least about 10 mg/day, e.g. at least about 10 mg in a treatment regime of once daily treatment, at least about 5 mg twice daily, at least about 3.3 mg thrice daily, etc.).

A dose of at least about 10 mg/day may be a dose of at least about 15 mg/day, at least about 20 g/day, at least about 25 mg/day. In some embodiments, the dose is 25±5 mg/day.

The total amount of $A_3AR$ ligand given a day to a patient, irrespective of the number of administrations is referred to herein as a "daily treatment dose".

Thus, in one embodiment, $A_3AR$ ligand is formulated in a unit dosage form for administering of the daily treatment dose of at least 10 mg/day. Where the dosage form is intended for administering to a patient in a treatment regimen comprising n doses per day, then a unit dosage form may comprise 1/n portion of the daily treatment dose (e.g., where the intended daily treatment dose is 20 mg and the treatment regimen is twice daily then each unit dosage form will have a dose of 10 mg; or where the intended daily treatment dose is 25 mg and the treatment regimen is twice daily then each unit dosage form will have a dose of 12.5 mg).

As used herein, the forms "a", "an" and "the" include singular as well as plural references unless the context clearly dictates otherwise. For example, the term "an $A_3AR$ ligand" includes one or more compounds which are capable of specifically affecting, directly or indirectly, fully or partially, the activity of the $A_3AR$.

Further, as used herein, the term "comprising" is intended to mean that the composition include the recited active agent, i.e. $A_3AR$ ligand, but not excluding other elements, such as physiologically acceptable carriers and excipients as well as other active agents. The term "consisting essentially of" is used to define compositions which include the recited elements but exclude other elements that may have an essential significance on treatment of fat accumulation. "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the $A_3AR$ ligand as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

NON-LIMITING EXAMPLES

Example 1—Effect of CF102 on Level of ALT and TG

Male C57BL/6 mice were used as a murine experimental model.

The $A_3AR$ agonist, 2-Chloro-$N^6$-(3-iodobenzyl)-adenosine-5'-N-methyluronamide (Cl-IB-MECA, referred to herein by the abbreviated name CF102), was synthesized for Can-Fite BioPharma by Albany Molecular Research Inc, Albany. N.Y., USA. CF102 was used in liquid form, dissolved in dimethyl sulfoxide (DMSO), used as the vehicle. Dissolved CF102 and the DMSO vehicle were administered at the same volume.

Male C57BL/6 mice were injected with a single subcutaneous injection of 200 μg streptozotocin (STZ) two days after birth and feeding with high fat diet after 4 weeks of age. At 6 weeks of age, the mice were randomized into vehicle and CF102 200 mg/kg treatment groups, given orally thrice daily. Treatment was given between 6 weeks of age and 9 weeks of age.

After Study termination, liver weight was measured and Liver-to-Body weight ratio was calculated.

Plasma ALT and liver triglyceride were measured and histological analyses were made on the liver sections for the following: Hematoxylin & Eosin staining for estimation of NAFLD Activity score and Sirius red staining for estimation of fibrosis area.

Figure 1:
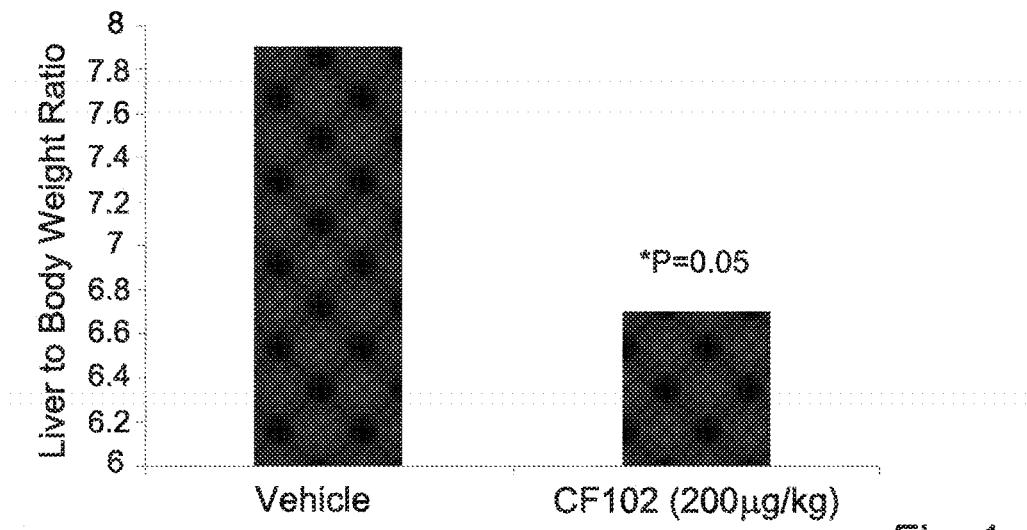
FIG. 1 is a bar graph showing the reduction of liver-to-body weight ratio in NASH livers in mice following daily administration of CF102 for three weeks as compared to non-treated mice (vehicle).
Figure 2A:
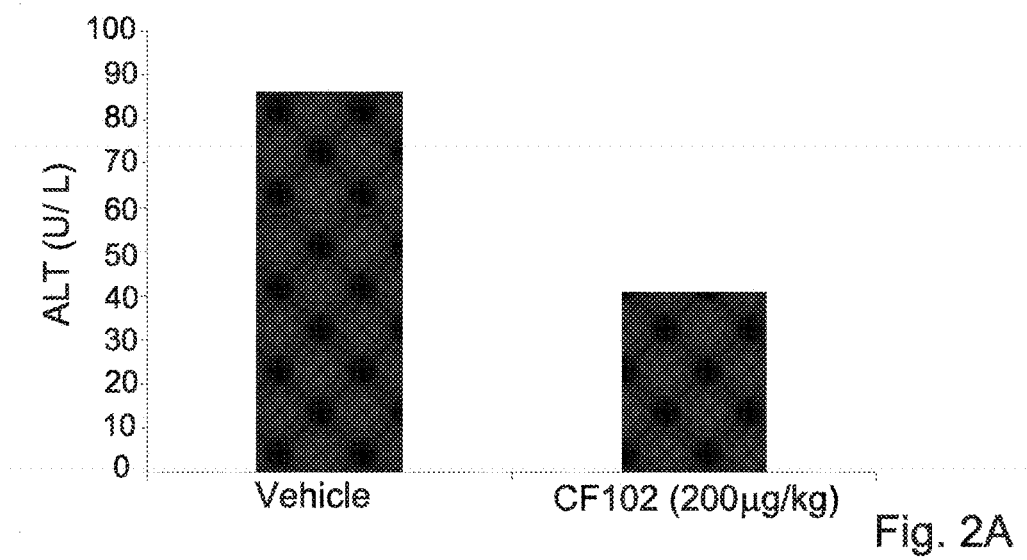
FIG. 2A-2B are bar graphs showing the decrease in plasma ALT level (FIG. 2A) and in triglyceride level (FIG. 2B) in NASH mice following daily administration of CF102 for three weeks as compared to non-treated mice (vehicle).
Figure 2B:
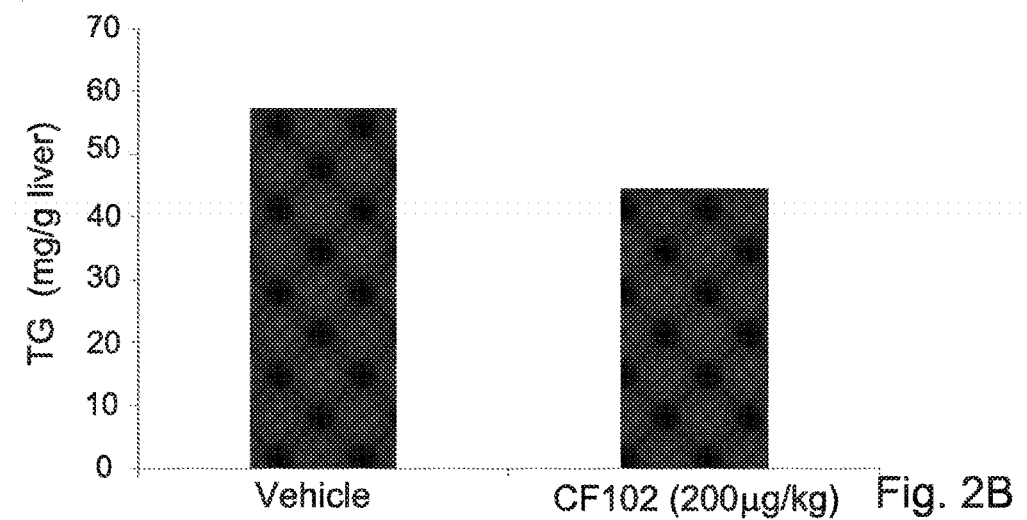

Results:

CF102 200 µg/kg reduced liver-to-body weight ratio in NASH livers (p=0.05) (FIG. 1). Furthermore, CF102 decreased ALT levels (FIG. 2A) and Triglycerides levels in the liver (FIG. 2B).

Figure 3A:
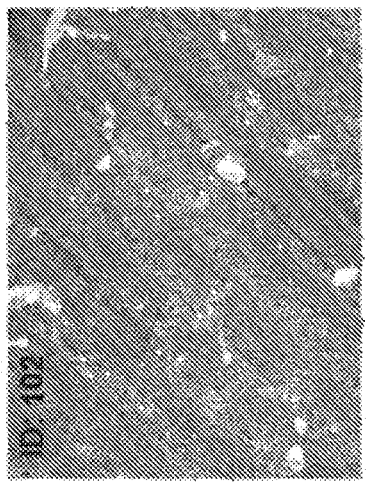
FIG. 3A-3D are histological liver sections from the CF102 treated groups at two different magnifications, ×50 and ×200 (FIGS. 3A and 3B respectively) and vehicle (DMSO) treated group (FIGS. 3C and 3D respectively).
Figure 3C:
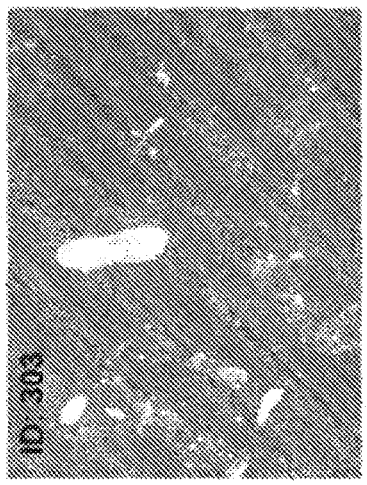
Figure 3B:
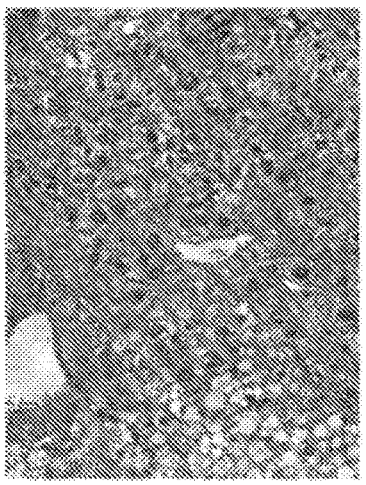
Figure 3D:
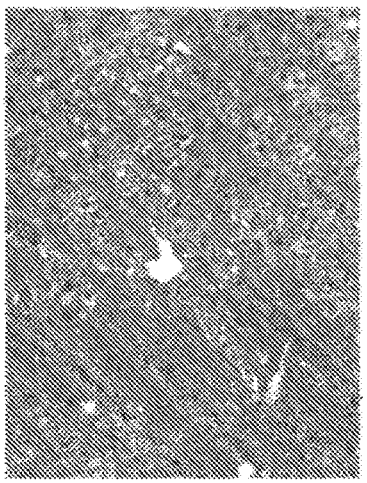

Liver sections from the Vehicle group exhibited severe micro- and macrovesicular fat deposition, hepatocellular ballooning and inflammatory cell infiltration. The CF102 treatment group showed a significant decrease in steatosis, ballooning and lobular inflammation compared to the Vehicle (FIGS. 3C and 3D, FIG. 4, respectively).

Example 2—Effect of CF102 on NAS Score

Male mice were injected with 200 µg/animal STZ two days after birth. From 4 weeks of age, the mice were fed with high fat diet. At 6 weeks of age, the mice were randomized into vehicle and CF102 200 µg/kg treatment groups. Treatment was given orally, thrice daily. Termination was performed after 9 weeks.

Hematoxylin & Eosin staining was used for estimation of NAFLD Activity.

Results:

CF102 (200 µg/kg) reduced the inflammation NAS (NAFLD Activity Score) score compared to the vehicle (FIG. 5).

The invention claimed is:

1. A method for treating a subject having a fibrotic liver tissue, the method comprises administering to said subject an amount of Cl-IB-MECA effective in reducing fibrosis area in said liver tissue, to a level indicative of a non-fibrotic tissue as evidenced by Sirius red staining, wherein said fibrotic liver tissue comprises progressive fibrosis.

2. The method of claim 1, administering said Cl-IB-MECA to a subject having a NAFLD Activity Score (NAS) indicative of a nonalcoholic steatohepatitis (NASH) liver along with said fibrotic liver tissue.

3. The method of claim 1, wherein said administration comprises oral administration of said Cl-IB-MECA.

4. The method of claim 1, wherein said administration comprises a daily treatment with an amount of at least about 10 mg/day.

5. The method of claim 4, wherein said administration is once a day.

6. The method of claim 4, wherein said administration is with an amount of 5 mg, twice daily.

7. The method of claim 1, comprises chronic treatment of said subject.

8. The method of claim 1, wherein the amount of Cl-IB-MECA is 25±5 mg/day.

* * * * *